United States Patent [19]

Mylari et al.

[11] Patent Number: 4,900,844
[45] Date of Patent: Feb. 13, 1990

[54] INTERMEDIATES FOR THE PREPARATION OF OXOPHTHALAZINYL ACETIC ACIDS HAVING BENZOTHIAZOLE OR OTHER HETEROCYCLIC SIDE CHAINS

[75] Inventors: Banavara L. Mylari, Waterford; William J. Zembrowski, Oakdale, both of Conn.

[73] Assignee: Pfizer Inc., New York, N.Y.

[21] Appl. No.: 354,521

[22] Filed: May 19, 1989

Related U.S. Application Data

[60] Division of Ser. No. 165,338, Mar. 8, 1988, Pat. No. 4,868,301, which is a continuation-in-part of Ser. No. 59,899, Jun. 9, 1987, abandoned.

[51] Int. Cl.[4] ............................................ C07D 493/02
[52] U.S. Cl. ..................................... 549/299; 549/305
[58] Field of Search ................................ 549/299, 305

[56] References Cited

U.S. PATENT DOCUMENTS 4,350,813  12/1982  Takei et al. ........................ 544/237
4,558,142  12/1985  Hollard et al. ...................... 549/465

Primary Examiner—Mary C. Lee
Assistant Examiner—Richard Sharpe
Attorney, Agent, or Firm—Peter C. Richardson; Paul H. Ginsburg; Gezina Holtrust

[57] ABSTRACT

A process for the preparation of oxophthalazinyl acetic acids having benzothiazole or other heterocyclic side chains comprising reacting an oxophthalizinyl acetic acid ester with an aniline derivative is disclosed. Also disclosed are processes for the preparation of such oxopthalizinyl esters.

2 Claims, No Drawings

INTERMEDIATES FOR THE PREPARATION OF OXOPHTHALAZINYL ACETIC ACIDS HAVING BENZOTHIAZOLE OR OTHER HETEROCYCLIC SIDE CHAINS

REFERENCE TO RELATED APPLICATION

This is a division of application Ser. No. 165,338, filed on Mar. 8, 1988 now U.S. Pat. No. 4,868,301, which is a continuation-in-part of U.S. Ser. No. 59,899, filed June 9, 1987, now abandoned.

BACKGROUND OF THE INVENTION

The present invention relates to the preparation of oxophthalazinyl acetic acids having benzothiazole or other heterocyclic side chains. Such compounds function as aldose reductase inhibitors and are useful in the treatment of certain chronic complications arising from diabetes mellitus, such as diabetes cataracts, retinopathy and neuropathy.

SUMMARY OF THE INVENTION

The present invention relates to a process for the preparation of a compound of the formula

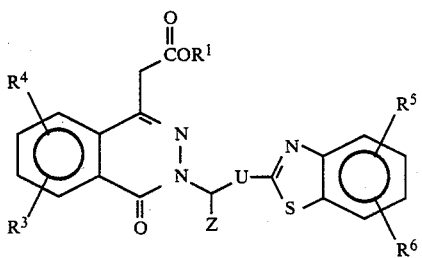
VIII wherein $R^1$ is hydrogen or $C_1$ to $C_4$ alkyl; $R^3$ and $R^4$ are the same or different and are hydrogen, fluoro, chloro, bromo, trifluoromethyl, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, or nitro, or $R^3$ and $R^4$ taken together are $C_1$-$C_4$ alkanedioxy; $R^5$ and $R^6$ are the same or different and are hydrogen, flouro, chloro, bromo, trifluoromethyl, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, nitro, or benzo or $R^5$ and $R^6$ taken together are $C_1$-$C_4$ alkanedioxy; Z is hydrogen or methyl; and U is S, $CH_2$ or a covalent bond, comprising reacting a compound of the formula

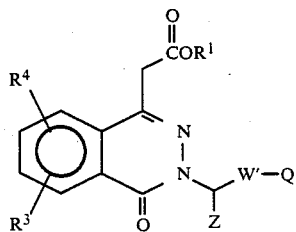
VI wherein $R^1$, $R^3$, $R^4$ and Z are as defined above, W' is S, $CH_2$ or a covalent bond, and Q is —CN or

wherein $R^2$ is $C_1$-$C_4$ alkyl, or an acid salt thereof with a compound of the formula

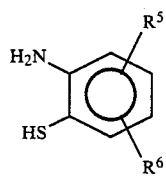
VII wherein $R^5$ and $R^6$ are defined above, or with an acid addition salt thereof, with the proviso that when neither one of said compounds of the formula VI and formula VII are in the form of its acid addition salt when it is added to the other of said compounds, the reaction is conducted in the presence of a strong acid; and, if desired, hydrolyzing a compound of the formula VIII wherein $R^1$ is other than hydrogen to the corresponding compound of the formula VIII wherein $R^1$ is hydrogen. The compounds of the formula VI wherein Q is

and all compounds of the formula VII may form acid addition salts. Although, we do not wish to be bound by theory, we believe that the addition of a strong acid to the aforementioned reaction mixture results in the formation in situ of an acid addition salt of at least one (and possibly both) of the compounds of the formula VI and formula VII and that the acid addition salt subsequently reacts with the other compound. Thus, at least one of the reactants is an acid addition salt that is performed or formed in situ.

The present invention also relates to the foregoing compounds of the formula VI, to processes for preparing intermediates useful in the preparation of compounds of the formula VI, to intermediates useful in preparing compounds of the formula VI, and to other processes wherein such intermediates are useful.

DETAILED DESCRIPTION OF THE INVENTION

The aforementioned compound of the formula VI wherein Q is —CN may be prepared by reacting a compound of the formula

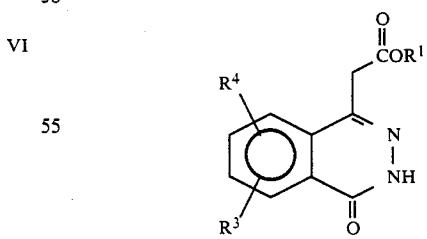
IV wherein $R^1$, $R^3$ and $R^4$ are as defined for formula VIII, with a compound of the formula

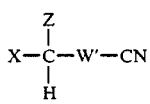

wherein X is chloro, bromo, —OSO₂—(C₁ to C₄ alkyl), or —OSO₂-aryl wherein aryl is phenyl, naphthyl, substituted phenyl, or substituted naphthyl, wherein the substituents on the substituted phenyl and substituted naphthyl groups are $C_1$ to $C_4$ alkyl, halogen or nitro; Z is hydrogen or methyl and W' is $CH_2$ or a covalent bond in the presence of a suitable base. The base should be of sufficient strength to catalyze the desired nucleophilic displacement. Examples of suitable bases include alkali metal hydrides (e.g., sodium hydride), alkali metal carbonates (e.g., potassium carbonate) alkali metal hydroxides (e.g., sodium hydroxide or potassium hydroxide), and alkali metal alkoxides (e.g., potassium tert-butoxide or sodium methoxide). A suitable solvent for this reaction is DMF (dimethylformamide). The reaction temperature is preferably about 20° to about 100° C., more preferably about 40° C.

Alternatively, the compound of the formula VI wherein W' is a covalent bond, Z is hydrogen and Q is —CN may be prepared by reacting a compound of the formula

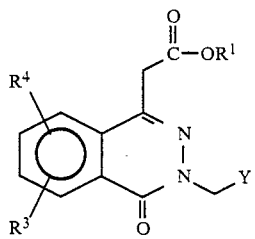

wherein Y is chloro or bromo; and $R^1$, $R^3$ and $R^4$ are as defined for formula VIII, with an alkali metal cyanide or alkaline earth metal cyanide. Examples of suitable cyanides include sodium and potassium cyanide. Suitable solvents include $C_1$-$C_4$ alcohols, $C_1$-$C_4$ alkanones and polar aprotic solvents e.g., DMF. The reaction temperature is preferably about 0° to about 40° C., more preferably about 20° C.

Compounds of the formula VI wherein W' is sulfur, Z is hydrogen and Q is —CN may be prepared by reacting a compound of the formula V wherein Y is chloro or bromo; and $R^1$, $R^3$ and $R^4$ are as defined for formula VIII, with an alkali metal or ammonium thiocyanate. Suitable solvents include $C_1$-$C_4$ alcohols, $C_1$-$C_4$ alkanones and polar aprotic solvents, e.g., DMF. The reaction temperature is preferably about 0° to about 40° C., more preferably about 20° C.

Compounds of the formula V where Y is chloro or bromo are, in turn, prepared from compounds of the formula V wherein Y is hydroxy by reaction with phosphorous trichloride or phosphorous tribromide at a temperature of about 0° to about 40° C., preferably about 20° C.

The aforementioned compound of the formula IV may be prepared by reacting a compound of the formula

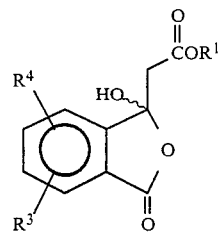

wherein $R^1$ is as defined above, with $NH_2NH_2$.

Alternatively, the compound of the formula II may be reacted with a strong acid (e.g., sulfuric acid or p-toluene sulfonic acid) to form a compound of the formula

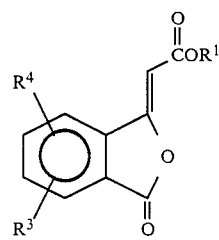

wherein $R^1$ is as defined for formula VIII, and the compound of formula III may be reacted with $NH_2NH_2$ to form a compound of formula IV.

Compounds of the formula V wherein Z is H, W is a covalent bond and Y is chloro or bromo are also useful in preparing compounds of the formula

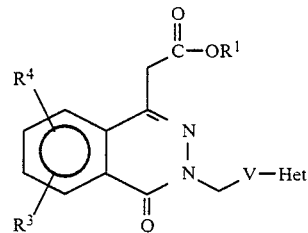

wherein $R^1$, $R^3$ and $R^4$ are as defined above for formula VIII; V is oxygen, sulfur or NH; and Het is a heterocyclic 5-membered ring having one nitrogen, oxygen or sulfur, two nitrogens one of which may be replaced by oxygen or sulfur, or three nitrogens one of which may be replaced by oxygen or sulfur, said ring substituted by one or two fluoro, chloro, $C_1$-$C_4$ alkyl or phenyl or condensed with benzo, or substituted by one of pyridyl, furyl or thienyl, said phenyl or benzo optionally substituted by one of iodo or trifluoromethylthio, or one or two of fluoro, chloro, bromo, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, or trifluoromethyl, and said pyridyl, furyl or thienyl optionally substituted in the 3-position by fluoro, chloro, bromo, $C_1$-$C_4$ alkyl or $C_1$-$C_4$ alkoxy; a heterocyclic 6-membered ring having one to three nitrogen atoms, or one to two nitrogen atoms and one oxygen or sulfur, and said ring substituted by one or two $C_1$-$C_4$ alkyl or phenyl, or condensed with benzo, or substituted by one of pyridyl, furyl or thienyl, said phenyl or benzo optionally substituted by one of iodo or trifluoromethylthio, or one or two of fluoro, chloro, bromo, $C_1$-$C_4$ alkyl, $C_1$-$C_4$ alkylthio, $C_1$-$C_4$ alkylsulfinyl, $C_1$–$C_4$ alkylsulfonyl, or trifluoromethyl, and said pyridyl, furyl or thienyl optionally substituted in the 3-position by fluoro, chloro, $C_1$–$C_4$ alkyl or $C_1$–$C_4$ alkoxy; oxazole or thiazole condensed with a 6-membered aromatic group containing one or two nitrogen atoms or with thiophene or furane, each optionally substituted by one of fluoro, chloro, bromo, trifluoromethyl, methylthio or methylsulfinyl; imidazolopyridine; naphthothiazole; or naphthoxazole. Such compounds are disclosed in U.S. Ser. No. 916,127, filed Oct. 7, 1986. The foregoing compounds of the formula X are prepared by reacting a compound of the formula V wherein Z is hydrogen, W is a covalent bond and X is chloro or bromo with an appropriate heterocycle containing an OH, SH, or $NH_2$ group in an aqueous, alcoholic, or polar aprotic solvent. Examples of suitable solvents include ethanol and DMF. The reaction may be catalyzed by a suitable base. The base should be of sufficient strength to catalyze the desired nucleophilic displacement. Examples of suitable bases include alkali metal hydrides (e.g., sodium hydride), alkali metal carbonates (e.g., potassium carbonate), alkali metal hydroxides (e.g., sodium hydroxide or potassium hydroxide) and alkali metal alkoxides (e.g., potassium tert-butoxide or sodium methoxide). The reaction temperature is preferably about 30° to about 100° C., preferably about 40° C.

The processes of the present invention are illustrated by the following reaction scheme:

Scheme 1

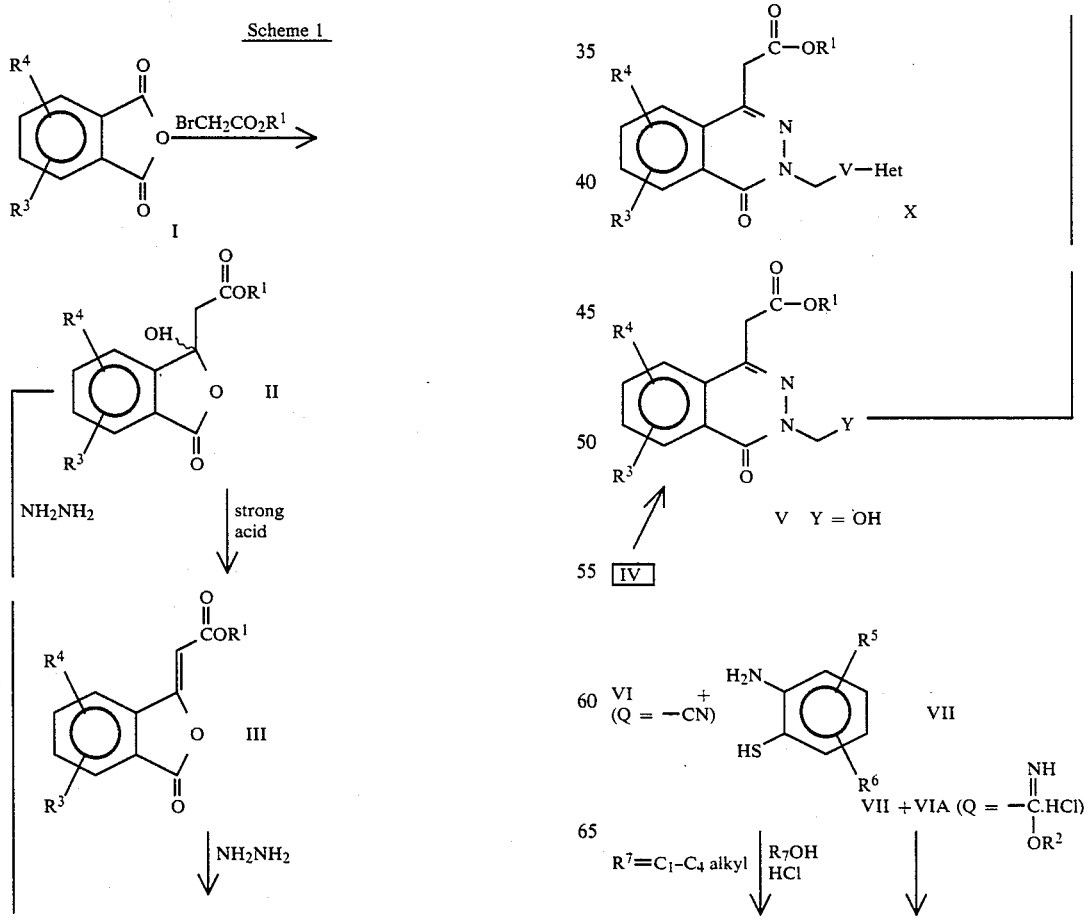

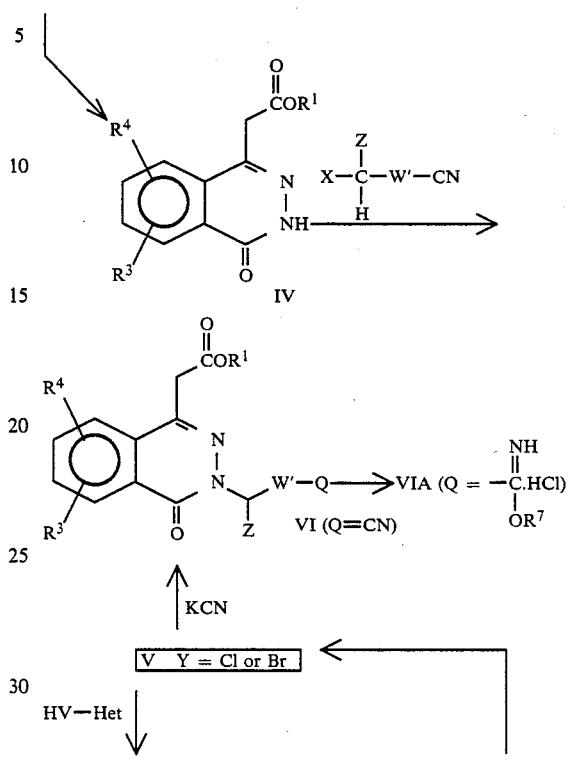

-continued
Scheme 1

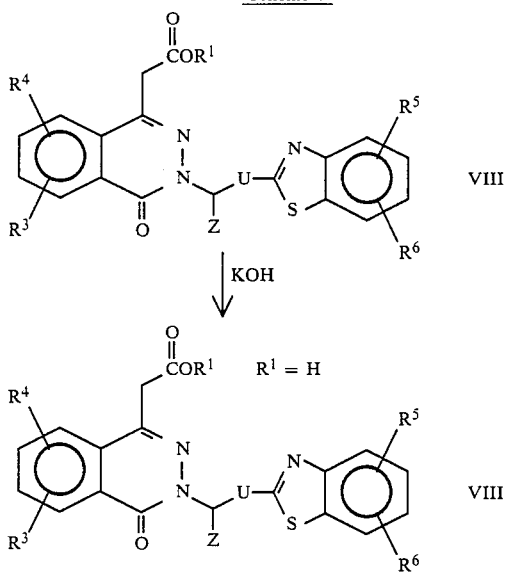

VIII

↓ KOH

VIII

A compound of the formula I is converted to a compound of the formula II using standard Reformatsky reaction conditions with zinc or a zinc-copper couple or using a variety of well-known modifications of the Reformatsky reaction (see, for example *Tetrahedron Letters*, 2569 (1984)). Suitable solvents for the conversion of the compound of formula I to the compound of formula II include aromatic hydrocarbons (e.g., benzene) and dialkyl ethers and cyclic ethers (e.g., tetrahydrofuran). The temperature is preferably maintained at about 35° to about 100° C., more preferably at reflux.

A compound of the formula II is converted to a compound of the formula III in the presence of a strong acid in a compatible solvent or without the use of a solvent. When a solvent is used, it is preferred that the solvent be a hydrocarbon solvent (e.g., benzene or toluene) and that the acid be an organic acid (e.g., p-toluenesulfonic acid). When such conditions are used, the temperature should preferably be at least about 90° C., more preferably, about 90° to about 100° C. The reaction mixture may conveniently be maintained at the reflux temperature of the reaction mixture.

When it is desired to convert a compound of the formula II to a compound of the formula III without using a solvent, it is preferred to use as the acid sulfuric acid at a temperature of about 0° to about 30° C., more preferably about 0° to about 20° C.

The conversion of a compound of the formula II or III to a compound of the formula IV may be accomplished with anhydrous or aqueous hydrazine in an alcoholic solvent (e.g., ethanol) at a temperature of about 20° to about 80° C., preferably about 60° C. Thus, the temperature may be room temperature or the reflux temperature of the solvent.

A compound of the formula IV may be converted to a compound of the formula V where Y is OH as described in *Tetrahedron*, 531 (1964). The reaction temperature is preferably about 20° to about 100° C., more preferably about 30° to about 40° C.

In order to prepare a compound of the formula VIII wherein $R^1$ is $C_1-C_4$ alkyl, a compound of the formula VI wherein Q is —CN may be reacted with a preformed acid addition salt of a compound of the formula VII (e.g., a hydrochloride salt) or with an acid addition salt prepared in situ, for example, by the addition of a strong acid such as hydrochloric acid. In practice, it is convenient to use the preformed acid addition salt. The solvent is preferably a $C_1$ to $C_4$ alkanol (e.g., ethanol) but mixtures of at least one molar equivalent of $C_1-C_4$ alkanol with a hydrocarbon or halocarbon solvent may be used. Examples of hydrocarbon and halocarbon solvents include benzene and chloroform, respectively. The temperature is preferably at least about 60° C. The reaction mixture is conveniently maintained at reflux temperature.

When the foregoing reaction is carried out in $C_1-C_4$ alkanol solvents (e.g. ethanol), the resulting compound of the formula VIII wherein $R^1$ is $C_1-C_4$ alkyl can be hydrolyzed in situ directly to the compound of the formula VIII wherein $R^1$ is H. The hydrolysis may be accomplished by adding an aqueous solution of a base such as sodium hydroxide or potassium hydroxide. The temperature is preferably about 20° to about 100° C., preferably about 60° C.

If a compound of the formula VIII is prepared in a solvent other than a $C_1-C_4$ alkanol, the compound may be isolated, dissolved in a $C_1-C_4$ alkanol, and then hydrolyzed as described above.

The preparation of a compound of the formula VIII may also be carried out by co-melting a mixture of a compound of the formula VI with a preformed acid addition salt of a compound of the formula VII (e.g., a hydrochloride salt) at a temperature between about 110° and about 180° C.

In another method, compound of the formula VIII may be prepared by reacting a compound of the formula VI wherein Q is

wherein $R^2$ is $C_1-C_4$ alkyl (hereinafter also referred to as a compound of the formula VIA) with a compound of the formula VII either as is or as in the form of an acid addition salt (e.g. hydrochloride salt). The reaction may be carried out in alcoholic, hydrocarbon or halocarbon solvents. Examples of such solvents include ethanol, toluene and chloroform, respectively. The reaction temperature is preferably at least about 60° C. The reaction mixture is conveniently maintained at a reflux temperature. Alternatively the reaction may be carried out by co-melting a mixture of the compound of the formula VIA with a compound of the formula VII at a temperature between about 110° and about 180° C.

The compound of the formula VIA may be prepared by reacting a compound of the formula VI with a $C_1-C_4$ alkanol in the presence of a mineral acid or organic acid. A preferred example of a mineral acid is gaseous hydrogen chloride. An example of an organic acid is p-toluene sulfonic acid. The reaction may be carried out at a temperature of about −5° C. up to about 40° C. If desired, the compound of the formula VIA may be prepared without adding an acid to the reaction mixture. In such a case, the reaction of the compound of the formula VIA and the compound of the formula VII should be conducted in the presence of a strong acid.

The reactions described above may be carried out at a pressure of about 0.5 to about 2 atmospheres (preferably at a pressure of about 1 atmosphere).

The compounds of formula VIII wherein $R^1$ is H and the pharmaceutically acceptable salts thereof are useful as inhibitors of the enzyme aldose reductase in the treatment of chronic complications of diabetes, such as diabetic cataracts, retinopathy and neuropathy. The compounds may be administered to a subject in need of treatment by a variety of conventional routes of administration, including orally, parenterally and topically. In general, these compounds will be administered orally or parenterally at dosages between about 0.5 and 25 mg/kg. body weight of the subject to be treated per day, preferably from about 1.0 to 10 mg/kg. However, some variation in dosage will necessarily occur depending on the condition of the subject being treated.

The following non-limiting Examples are illustrative of the present invention. All melting points are uncorrected.

EXAMPLE 1

Ethyl-1,3-dihydro-1-hydroxy-3-oxo-1-isobenzofuran acetate

Procedure A

To a refluxing slurry of zinc dust (37.0) in benzene (250 ml) was added a portion (15 ml) of a solution of ethyl bromoacetate (8.35 g) and phthalic anhydride (7.4 g) in benzene (250 ml). Following an exothermic reaction during this addition, the remaining portion of the benzene solution was added and the refluxing continued for 8 hours. The reaction mixture was cooled to room temperature and was then poured onto aqueous sulfuric acid (100 ml, 10%) and the organic layer was collected. This organic layer was sequentially washed with water (2×50 ml), aqueous sodium bicarbonate (25 ml, 10% by weight) and finally with water (25 ml). The washed organic extract was dried and evaporated. The resulting crude product was purified by chromatography (yield: 12.84 g; $^1$HNMR(CDCl$_3$, 60 MHz); 1.25 (t, J-8 Hz, 3H), 3.15 (s, 2H), 4.2 (9, J=8 Hz, 2H), 6.25 (broad, 1H), 7.6 (M, 4H)).

Procedure B

To a refluxing suspension of zinc-copper couple (31.0 g) in tetrahydrofuran (50 ml) was gradually added a solution of phthalic anhydride (29.6 g) and ethyl bromoacetate (13.1 g) in tetrahydrofuran (150 ml). The reaction mixture was refluxed for 2 hours and it was then cooled and filtered. The filtrate was added to aqueous HCl (200 ml, 10% by volume) and then extracted with ethyl acetate (3×5 ml). The ethyl acetate layer was washed with water (2×50 ml) and evaporated to a clear colorless oil (yield: 18.2 g; $^1$HNMR as in Procedure A).

EXAMPLE 2 t-Butyl-1,3-dihydro-1-hydroxy-3-oxo-1-isobenzofuran acetate

Starting from phthalic anhydride (14.81 g), t-butyl bromoacetate (29.25 g), zinc-copper couple (15.0 G) and tetrahydrofuran (100 ml) and using the method of Procedure B, the title product was obtained (yield; 24.0 g). This product was further purified by chromatography ($^1$HNMR (CDCl, 250 MHz), 1.90 (s, 9H), 4.0 (s, 2H), 6.7–7.2 (m, 4H)).

EXAMPLE 3

(Z)-3-Ethoxycarbonylmethylidenaphthalide,

Ethyl-1,3-dihydro-3-oxo-1-isobenzofuran acetate (2.36 g) was dissolved in concentrated sulfuric acid (5 ml) and allowed to stand at room temperature for 5 minutes. It was then slowly poured onto ice-water (50 ml) and the resulting white precipitate was collected, washed with water (3×25 ml) and then air-dried (yield: 2.08 g; See *J. Org. Chem.*, 31, 4077, (1966).

EXAMPLE 4

Ethyl-4-oxo-3H-phthalazin-1-yl-acetate

To a solution of ethyl-1,3-dihydro-3-oxo-1-isobenzofuran acetate (4.72 g) in ethanol (20 ml) was added hydrazine (1.28 g) all in one portion. The resulting white precipitate was collected, washed with aqueous HCl (20 ml, 10% by volume) and then with water. The solid was air-dried to obtain the title compound (See U.S. Pat. No. 4,251,528).

EXAMPLE 5 t-Butyl-4-oxo-3H-phthalazin-1-yl-acetate

To a solution of t-butyl-1,3-dihydro-1-hydroxy-3-oxo-1-isobenzofuran acetate (7.92 g) in ethanol (200 ml) was added hydrazine hydrate (5.0 ml, 85% by weight) and then refluxed for 1 hour. The precipitated white solid was collected, washed with water (2×25 ml) and then air-dried (yield: 5.30 g; m.p. 164°–166° C.).

EXAMPLE 6

Methyl-3-cyanomethyl-4-oxo-3-H-phthalazin-1-ylacetate

Procedure A

To a mixture of methyl-4-oxo-3-H-phthalazin-1-ylacetate (5.45 g) in dimethylformamide (25 ml) was added dry potassium t-butoxide (2.95 g) all in one portion. To the resulting dark green solution was gradually added chloroacetonitrile (1.89 g). The reaction mixture was stirred for 30 minutes and was the poured onto ice water (100 ml). Sufficient 10% HCl (by volume) was added to adjust the pH of the resulting mixture to about 4.0 and the precipitated off-white solid was collected and air-dried (yield: 5.74 g; m.p. 118°–119° C.).

Procedure B

Procedure A was repeated as above except that chloroacetonitrile was replaced by bromoacetonitrile (3.0 g). The title product was obtained in 4.93 g yield with the same melting point as the product of Procedure A.

Procedure C

Procedure A was repeated on twice the scale but chloroacetonitrile was replaced by cyanomethyl benzenesulfonate (10.90 g). The title product was obtained in 10.98 g yield.

EXAMPLE 7

Ethyl-3-cyanomethyl-4-oxo-3-H-phthalazin-1-ylacetate

Procedure A

To a solution of ethyl-4-oxo-3-H-phthalazin-1-yl acetate (11.31 g) and dry potassium t-butoxide (5.9 g) in dimethylformamide (50 ml) was added chloroacetonitrile (3.78 g) ad the solution was stirred for 30 minutes. This solution was poured onto ice water (300 ml); sufficient 10% HCl was added to adjust the pH of the resulting mixture to about 4.0 and the precipitated solid was collected and air-dried (yield: 11.81 g; m.p. 113°–114° C.).

Procedure B

Chloroacetonitrile (3.0 ml) as added to a solution of ethyl 4-oxo-3H-phthalazin-1-ylacetate (10.0 g) in dimethylformamide (100 ml) containing anhydrous potassium carbonate (9.0 g) and the mixture was stirred overnight. It was then poured onto ice-water (500 ml); sufficient 10% HCl was added to adjust the pH to about 4.0 and the precipitated solid was obtained upon air drying (yield: 9.7 g; m.p. 113°–114° C.).

Procedure C

A mixture of ethyl-4-oxo-3H-phthalazin-1-ylacetate (5.0 g), potassium carbonate (4.5 g), acetone (100 ml) and chloroacetonitrile (2.0 ml) was refluxed overnight. The reaction mixture was then worked-up as in Procedure B (yield: 4.1 g).

Procedure D

To an ice-cold solution of ethyl-3-bromomethyl-4-oxo-3-H-phthalazin-1-ylacetate (2.43 g) in acetone (3.5 ml) was added dropwise a solution of potassium cyanide (0.49 g) and potassium iodide (2 mg) in water (3.5 ml). The reaction mixture was stirred for 2 hours and it was then poured onto ice water (200 ml). The precipitated solid was purified by chromatography on silica gel, eluting with 95% $CH_2Cl_2$-5% ethyl acetate (percents by volume) to obtain the title compound (yield: 1.54 g).

EXAMPLE 8

Ethyl-3-cyanoethyl-4-oxo-3-H-phthalazin-1-ylacetate

To a solution of ethyl-4-oxo-3-H-phthalazin-1-ylacetate (10.91 g) and dry potassium t-butoxide (5.90 g) in dimethylformamide (50 ml) was added 3-chloropropionitrile (4.92 g) and the resulting solution was stirred for 30 minutes. The solution was then poured onto ice-water (300 ml); sufficient 10% HCl was added to adjust the pH of the resulting mixture to about 4.0 and the precipitated solid was collected and crystallized from methanol (yield: 7.64 g; m.p. 125°–126° C.).

EXAMPLE 9

Ethyl-3-hydroxymethyl-4-oxo-3-H-phthalazin-1-ylacetate

A mixture of ethyl-4-oxo-3-H-phthalazin-1-ylacetate (23.42 g), ethanol (200 ml) and aqueous formaldehyde (37% concentration, 100 ml) was refluxed for 40 hours. This solution was concentrated to 100 ml and was then poured onto ice water (750 ml). The precipitated solid was collected and air-dried (yield: 17.1 g; m.p. 113°–114° C.).

EXAMPLE 10

Methyl-3-hydroxymethyl-4-oxo-3-H-phthalazin-1-ylacetate

A mixture of methyl-4-oxo-3-H-phthalazin-1-ylacetate (2.18 g), methanol (50 ml) and aqueous formaldehyde (37% concentration, 10 ml) was refluxed for 40 hours. The reaction mixture was cooled to room temperature and then poured onto water (50 ml). The resulting solid was collected and crystallized from methanol (yield: 0.5 g; m.p. 154°–155° C.).

EXAMPLE 11

Ethyl-3-bromomethyl-4-oxo-3-H-phthalazin-1-ylacetate

A solution of ethyl-3-hydroxymethyl-4-oxo-3-H-phthalazin-1-ylacetate (13.1 g), phosphorous tribromide (13.5 g) and anhydrous ether (250 ml) was stirred overnight at room temperature. It was then poured onto water (200 ml). The organic layer was collected, washed again with water (3×100 ml) and then dried over anhydrous sodium sulfate. The dried organic extract was evaporated to dryness and the resulting crude solid was purified by chromatography on silica gel, eluting with 95% $CH_2Cl_2$-5% ethyl acetate (percents by volume) to obtain the title compound (yield: 9.8 g; m.p. 96° C.).

EXAMPLE 12

Methyl-3-bromomethyl-4-oxo-3-H-phthalazin-1-ylacetate

A solution of methyl-3-hydroxymethyl-4-oxophthalazin-1-ylacetate (0.49 g), phosphorous tribromide (0.54 g) and methylene chloride (10 ml) was stirred at room temperature for 2 hours. The solution was poured onto ice-water (5 ml) and the separated methylene chloride layer was collected, dried and evaporated to obtain a light yellow solid (yield: 0.43 g; m.p. 98°–104° C.).

EXAMPLE 13

Ethyl-3-Chloromethyl-4-oxo-3-H-phthalazin-1-ylacetate

A solution of ethyl-3-hydroxymethyl-4-oxo-3-H-phthalazin-1-ylacetate (1.31 g) and methanesulfonyl chloride (0.69 g) in methylene chloride (10 ml) containing pyridine (0.8 ml) was stirred at room temperature overnight. Upon evaporation of methylene chloride and purification of the residue by chromatography on silica gel, eluting with a mixture of a chloroform and ethyl acetate (9:1), the title product was obtained (yield: 0.51 g; m.p. 99°–100° C.).

Alternatively, follow the procedure in Example 11, but substitute phosphorous trichloride for phosphorous tribromide, to obtain the title compound.

EXAMPLE 14

Ethyl-3-(5-trifluoromethylbenzothiazol-2-ylmethyl)-4-oxo-3-H-phthalazin-1-ylacetate

Procedure A

A mixture of ethyl 3-cyanomethyl-4-oxophthalazin-1-ylacetate (2.71 g), 2-amino-4-trifluoromethyl-thiophenol hydrochloride (2.40 g) and ethanol (20 ml) was refluxed for 8 hours. The heavy precipitate obtained upon cooling was filtered and the collected solid was air-dried to obtain the title compound (yield: 4.3 g; m.p. 136° C.).

Procedure B

A mixture of ethyl 3-cyanomethyl-4-oxo-phthalazin-1-ylacetate (0.27 g) and 2-amino-4-trifluoromethyl-thiophenol hydrochloride (0.23 g) was heated to a melt at 180° C. for 10 minutes. The mobile liquid was cooled and then suspended in water. Filtration of the mixture gave the title compound in 75% yield.

EXAMPLE 15

Ethyl-3-(5,7-difluorobenzothiazol-2-ylmethyl)-4-oxo-3-H-phthalazin-1-ylacetate

A mixture of ethyl-3-cyanomethyl-4-oxo-phthalazin-1-ylacetate (1.29 g), 2-amino-4,6-difluoro-thiophenol hydrochloride (0.98 g) and ethanol (20 ml) was refluxed for 6 hours. Upon cooling, the title compound precipitated out as a pale yellow solid (yield: 1.62 g; m.p. 115°–117° C.).

EXAMPLE 16

3-(5-Trifluoromethylbenzothiazole-2-ylmethyl)-4-oxo-3-H-phthalazin-1-ylacetic acid

Procedure A

A mixture of ethyl-3-(5-trifluoromethylbenzothiazole-2-ylmethyl-4-oxo-3-H-phthalazin-1-ylacetate (5.0 g), methanol (60 ml), tetrahydrofuran (30 ml) and 10% aqueous potassium hydroxide (20 ml) was stirred for 10 minutes at room temperature. The solution was concentrated to a volume of 20 ml and was then diluted with water (50 ml). The resulting solution was acidified to pH about 4.0 by addition of sufficient 10% HCl. The precipitated off-white solid was collected and air-dried (yield: 4.8 g; m.p. 197°–198° C.).

Procedure B

A mixture of ethyl-3-cyanomethyl-4-oxophthalazin-1-ylacetate (2.71 g), 2-amino-4-trifluoromethyl-thiophenol hydrochloride (2.40 g) and ethanol (20 ml) was refluxed overnight. The reaction mixture was cooled to 40° C. and to it was added tetrahydrofuran (10 ml) and 5% aqueous potassium hydroxide (10 ml). The mixture was stirred for 1 hour at room temperature and the solvents were removed by evaporation. The residue was diluted with water (50 ml) and the resulting solution was extracted with ether (20 ml). The basic aqueous layer was collected and acidified to pH of about 4.0 by addition of sufficient 10% HCl. The precipitated solid was collected and air-dried (yield: 3.68 mg; m.p. 197°–198° C.).

EXAMPLE 17

3-(5,7-Difluorobenzothiazole-2-ylmethyl)-4-oxo-3-H-phthalazin-1-ylacetic acid

Ethyl 3-(5,7-difluorobenzothiazol-2-ylmethyl)-4-oxo-3-H-phthalazin-1-ylacetate (1.0 g) was hydrolyzed according to the method of Example 16, Procedure A, to obtain the title compound (m.p. 178° C.).

EXAMPLE 18

3-(5-Trifluoromethylbenzothiazole-2-ylethyl)-4-oxo-3-H-phthalazin-1-ylacetic acid A mixture of ethyl-3-cyanoethyl-4-oxo-3-H-phthalazin-1-ylacetate (2.71 g), 2-amino-4-trifluoromethyl-thiophenol hydrochloride (2.29 g) and ethanol (20 ml) was refluxed overnight. The crude product obtained upon evaporation of ethanol was purified by chromatography on silica gel, eluting with a mixture of hexane and tetrahydrofuran (4:1). The white solid obtained (0.3 g) was used directly in the next step which consisted of dissolving the compound in ethanol (20 ml) containing 5% aqueous KOH (2 ml) and stirring at room temperature for 2 hours. The ethanol was evaporated, the residue was diluted with water (10 ml), extracted with ether (2×10 ml) and the aqueous extract acidified to pH 2.0. The precipitated solid was collected and then crystallized from ethanol (yield: 0.12 g; m.p. 184°–185° C.).

EXAMPLE 19

Ethyl-3-(ethyl acetimidate)-4-oxo-3H-phthalazin-1-ylacetate, hydrochloride

Dry hydrogen chloride gas was passed for 5 minutes into a solution of 3-cyanomethyl-4-oxo-phthalazin-1-ylacetate (27.1 g) in dry tetrahydrofuran (200 ml) and absolute ethanol (5.9 ml). The precipitate formed upon letting the reaction stand at room temperature overnight was filtered off to obtain the desired product (13.05 g, m.p. 208°–210° C.).

EXAMPLE 20

Ethyl-3-(5-trifluoromethylbenzothiazole-2-ylmethyl)-4-oxo-3H-phthalazin-1-ylacetate A mixture of ethyl-3-ethyl acetimidate)-4-oxo-3H-phthalazin-1-ylacetate hydrochloride (0.35 g) and 2-amino-5-trifluoromethyl thiophenol hydrochloride (0.23 g) in toluene (20 ml) was refluxed for 16 hours. The precipitate obtained upon cooling was crystallized from ethanol to obtain the product (m.p. 136° C.).

EXAMPLE 21

Ethyl-3-thiocyanatomethyl-4-oxo-3-H-phthalazin-1-ylacetate

Following the method of Procedure D of Example 7, but replacing potassium cyanide by potassium thiocyanate, prepare the title compound.

We claim:

1. A compound of the formula

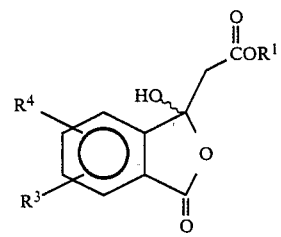

wherein $R^1$ is hydrogen or $C_1$ or $C_4$ alkyl; and $R^3$ and $R^4$ are the same or different and are hydrogen, fluoro, chloro, bromo, trifluoromethyl, $C_1$–$C_4$ alkyl, $C_1$–$C_4$ alkoxy, $C_1$–$C_4$ alkylthio, $C_1$–$C_4$ alkylsulfinyl, $C_1$–$C_4$ alkylsulfonyl, or nitro, or $R^3$ and $R^4$ taken together are $C_1$–$C_4$ alkylenedioxy.

2. A compound according to claim 1, wherein $R^3$ and $R^4$ are hydrogen and $R^1$ is ethyl or t-butyl.

* * * * *